United States Patent [19]
Singh et al.

[11] Patent Number: 5,686,661
[45] Date of Patent: Nov. 11, 1997

[54] IN-SITU, REAL TIME VISCOSITY MEASUREMENT OF MOLTEN MATERIALS WITH LASER INDUCED ULTRASONICS

[75] Inventors: Jagdish P. Singh, Starkville; Krishnan Balasubramaniam, Brandon; R. Daniel Costley, Starkville; Vimal V. Shah, Mississippi State; Christopher Winstead, Starkville, all of Miss.

[73] Assignee: Mississippi State University, Mississippi State, Miss.

[21] Appl. No.: 659,197

[22] Filed: Jun. 4, 1996

[51] Int. Cl.$^6$ .................. G01N 11/00; G01N 29/00; A61B 10/00
[52] U.S. Cl. .................. 73/54.41; 73/54.02; 73/655
[58] Field of Search .................. 73/54.41, 54.01, 73/54.02, 655

[56] References Cited

U.S. PATENT DOCUMENTS

| | | | |
|---|---|---|---|
| 2,966,058 | 12/1960 | McSkimin | 73/67.7 |
| 3,553,636 | 1/1971 | Baird | 340/1 |
| 4,149,405 | 4/1979 | Ringrose | 73/54 |
| 4,330,699 | 5/1982 | Farrow | 219/121 LD |
| 4,331,025 | 5/1982 | Ord, Jr. | 73/54 |
| 4,408,494 | 10/1983 | Koblanski | 73/646 |
| 4,441,358 | 4/1984 | Osborne | 73/55 |
| 4,677,842 | 7/1987 | Piché | 73/32 A |
| 4,691,714 | 9/1987 | Wong et al. | 128/738 |
| 4,721,874 | 1/1988 | Emmert | 310/333 |
| 4,779,452 | 10/1988 | Cohen-Tenoudji et al. | 73/54 |
| 4,862,384 | 8/1989 | Bujard | 364/509 |
| 4,920,787 | 5/1990 | Dual et al. | 73/54 |
| 5,005,401 | 4/1991 | Pierce et al. | 73/54 |
| 5,033,304 | 7/1991 | Rosen | 73/597 |
| 5,056,357 | 10/1991 | Dymling et al. | 73/54 |
| 5,186,040 | 2/1993 | Tissier et al. | 73/54.01 |
| 5,365,778 | 11/1994 | Sheen et al. | 73/54.41 |

FOREIGN PATENT DOCUMENTS

| | | |
|---|---|---|
| 2671102 | 12/1990 | France . |
| WO9010530-A | 3/1989 | WIPO . |
| WO9420021 | 2/1994 | WIPO . |

OTHER PUBLICATIONS

Abstract only of WO9420021 Feb. 21, 21, 1994; Summers, J.B.; World Organization.
Abstract only of Fr2671102 France Patent, Dec. 27, 1990; Jolivet, J. et al.
Abstract only of WO9010530–A Mar. 10, 1989; Hoelsoe, P. et al.; World Organization.

*Primary Examiner*—Hezron E. Williams
*Assistant Examiner*—J. David Wiggins
*Attorney, Agent, or Firm*—Oblon, Spivak, McClelland, Maier & Neustadt, P.C.

[57] ABSTRACT

This invention is directed to a method of remotely measuring the viscosity of molten materials such as melt glass, melt alloys, etc. during processing of the material.

14 Claims, 7 Drawing Sheets

IN-SITU, REAL TIME VISCOSITY MEASUREMENT OF MOLTEN MATERIALS WITH LASER INDUCED ULTRASONICS

BACKGROUND OF THE INVENTION

1. Field of the Invention

This invention is directed to a method of measuring the viscosity of a molten material such as a melt glass, a melt alloy, etc., which may be used during processing of the material.

2. Discussion of the Background

There has been extensive work done in the field of laser generated ultrasound. The work done in the measurement of viscosity by mechanical devices is well known and there are several visco-meters available in the market today. Other methods include air bubbles and methods using traditional piezo-electric ultrasound transducers for measuring viscosity.

Sheen et al., U.S. Pat. No. 5,365,778, reports the use of an ultrasonic viscometer for measuring fluid viscosity by measuring the reflections of ultrasonic shear and longitudinal waves. The method uses a two-interface fluid and air transducer wedge to measure relative signal changes and to enable self-calibration and uses a ratio of reflection coefficients from two different frequencies to compensate for environmental changes such as temperature. Reflected longitudinal waves are used to determine phase velocity (from which density is derived), while reflected shear wave coefficients determine the product of fluid density and viscosity. The fluid density component is subtracted out by measuring the longitudinal-wave phase velocity in the fluid and the reflection coefficient at the fluid-wedge interface.

Dymling et al., U.S. Pat. No. 5,056,357, reports a method of measuring the parameters of a mobile medium, by measuring the Doppler shift effects on ultrasound signals or on optical laser energy. In one embodiment a piezoelectric ultrasound transducer transits acoustic energy into a mobile medium. The frequency shift is measured in accordance with the Doppler effect and the viscosity determined if the signal intensity is known. If the medium contains bodies with an optical impedance, optical Doppler techniques, using optical laser Doppler can be used (column 6, lines 11–28).

McSkimin U.S. Pat. No. 2,966,058, reports a conventional ultrasonic viscosity measurement device using two transverse shear acoustic waves and measuring the reflected wave signals.

Baird U.S. Pat. No. 3,553,636, reports an ultrasonic viscosity measurement method of two stratified immiscible liquids, in which direct contact with the liquid is avoided. A transducer is mounted to a container wall and the attenuation of a reflected pulse is measured.

Dual et al. U.S. Pat. No. 4,920,787 reports a viscometer, which measures damping ratio of a vibrating resonator and a piezoelectric transducer. The frequency of the transducer is higher than that of the resonator. The reference refers to the measurement of the ratio of the frequency shift to the phase shift, however, this is appears to be a comparison of the resonator frequency and the transducer frequency.

Methods for the laser generation of ultrasound have been extensively developed, to the point where this technique is now being applied.

Farrow, U.S. Pat. No. 4,330,699, reports the use of a non-contact laser/ultrasonic welding technique for strengthening a common laser weld, by the addition of ultrasonic cavitation and cleaning. According to this process, a high powered laser applies heat to a weld joint to produce a melt, wherein the output of the laser, or a second laser is amplitude modulated to generate acoustic waves in the melt. This method improves interdiffusion of melt and the homogeneity of the weld joint, resulting in an improved quality of a laser weld.

Moshe, U.S. Pat. No. 5,033,304, reports a nondestructive inspection method and apparatus for determining fiber characteristics such as elasticity, diameter and chemical composition and the thickness and quality of fiber coatings via laser-generated ultrasound for velocity and attenuation measurements.

The generation of ultrasound, using pulse lasers has been reported (i.e., D. A. Hutchins "Ultrasonic Generation by Pulsed Lasers" in Physical Acoustics, vol:XVIII, (Eds. W. P. Mason and R. N. Thurston) (1988). Academic Press, N.Y. pp. 21–123). However, conventional ultrasonic viscometers, use a piezoelectric type transducer, which has a relatively narrow band frequency width, and the viscosity is determined by the reflection factor at different frequencies. In addition, the piezoelectric sensor which is generating ultrasound must be attached directly to the container of the molten medium, and does not allow for remote signal generation.

At present, the viscosity of molten materials is measured by mechanical viscometers. In most types of commercial viscometers, part of the instrument has to be inside the molten material which perturbs the molten material. This technique is not suitable in very high viscous melts and at very high temperatures.

Accordingly, while lasers have been reported in the generation of ultrasonic pulses, their use for determining the viscosity of a liquid has not been applied. Moreover, despite extensive work in the area of viscometry, and even ultrasonic viscometry, improved methods for measuring the viscosity of materials are being sought to overcome the drawbacks presently observed.

SUMMARY OF THE INVENTION

Accordingly, one embodiment of the present invention is a method of determining the viscosity of a molten material using ultrasound, generated from a pulsed laser source.

Accordingly, a second embodiment of the present invention is a method of determining the viscosity of a molten material using ultrasound, generated from a pulsed laser source, by measurement of the relationship of frequency with amplitude, phase or amplitude and phase.

Another embodiment of the present invention is an apparatus for determining viscosity comprising i) a pulsed laser source for producing ultrasonic longitudinal and shear waves; and ii) a detection means.

These and other embodiments of the present invention have been made possible by the discovery that ultrasonic waves, generated from a pulsed laser source are capable of providing information of the viscosity of a liquid and/or molten material. The use of frequency-amplitude and/or frequency-phase relationships of a laser generated ultrasound offers tremendous advantages in determining the viscosity. The frequency-amplitude and/or frequency-phase relationships enables the viscosity measurements for viscous materials, wherein conventional piezoelectric generated ultrasound is only generally effective at measuring low viscosity fluids.

The present invention offers the advantages that (a) Ultrasonic longitudinal and shear waves can be generated without physically contacting the material to be measured or its container and detected at material surfaces.

(b) Ultrasonic wave modes (especially shear modes) are sensitive to the viscosity of the material. The viscosity can be evaluated using a combination of measurements involving the wave velocity, the reflection factor, and the attenuation of both the shear and longitudinal wave modes of ultrasound, depending on the specific physical geometry of the container which holds the material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The generation of ultrasonic waves by pulsed lasers can be achieved by conventional means known to those of ordinary skill in the art. An example of a suitable technique is described in Scruby et al "Laser Generation of Ultrasound in Metals", Research Techniques in Nondestructive Testing, Vol. V, R, S, Sharpe ed., Academic Press (1982), pp 281–327.

The frequency of the ultrasound waves will generally depend upon the physical geometry of the container such as wall thickness as well as the range of viscosity being measured. If the wall thickness is high or if the viscosity range is high, then it is preferable to use a lower frequency ultrasound. The vice-versa is also true. Adjustment of the frequency is within the level of skill of one of ordinary skill in the art without undue experimentation.

The ultrasonic wave frequencies applicable to this method typically ranges from 100 Khz. to 30,000 Khz.

The frequency of the ultrasound is not particularly limited. Suitable frequencies range from 100 KHz to 20–30 MHz, preferably from 0.1–25 MHz, more preferably from 0.5 to 5 MHz.

The amplitude of the ultrasound generated should allow for travel through the container wall thickness, reflection at the wall-fluid interface and the travel back to the outer wall surface and should be of sufficient amplitude for detection by the detection means. Relevant factors which affect the amplitude are the wall material properties, wall thickness, surface finish of the inner/outer surface, and the sensitivity of the interferometer. Adjustment of the amplitude is within the level of skill of one of ordinary skill in the art without undue experimentation.

The intensity of the laser pulse is also adjusted to be sufficient to generate an ultrasonic wave with both shear and longitudinal wave components. However, the intensity of the laser pulse should not be so high so as to cause significant amounts of ablation of the material of the container. In addition, the power density will influence the type of ultrasonic wave being produced. At low laser power density, relatively more energy is contained in the shear wave mode than in the longitudinal waves. At higher laser power density, the number of shear waves is reduced such that there are more longitudinal than shear waves. The longitudinal wave reflection factor is much less sensitive to differences in viscosity than the shear wave reflection factor, and accordingly it is preferably to use a power intensity which produces more shear waves than longitudinal waves. A pulse energy of from about 10 milli joules to about 10 joules, preferably from 10–20 milli joules is preferred.

Ablation of the wall material due to the impingement of the pulsed laser should be avoided. Depending upon the wall material properties the power densities of the pulsed laser must be selected. A typical energy level for the pulsed laser is 1.0 million watts/square cm.

For example, an ultrasonic wave may be generated by applying a pulsed laser source to the wall of a container of a fluid. The energy from the laser pulse heats the material the container wall, causing the generation of shear and longitudinal waves.

The use of a pulsed laser source allows for remote generation of ultrasonic waves, from a power source external to the container of the material. However, the container wall produces the ultrasonic waves, acting as a transducer upon localized heating from the pulsed laser source.

A pulsed laser of almost any type can be used to generate ultrasonic waves. Suitable non-limiting examples include $CO_2$, krypton fluoride, neodymium yttrium-aluminum garnet (YAG), ruby, titanium sapphire, aluminum gallium arsenide, indium gallium arsenide phosphide, aluminum indium gallium phosphide, and various dye lasers. It is preferred that the laser source have a stable power output, as variations in power output can have an adverse affect on the precision of the method. If a laser source has an unstable power output, this can be compensated for by conducting multiple measurements and averaging the results.

The duration of a laser pulse is chosen sufficient to generate an ultrasonic wave. Suitable pulse durations are generally from 1 nanosecond up to 10 microseconds but preferably between 5–200 nanoseconds.

The ultrasonic waves are generated as a result of heating of the material of the container by the pulsed laser. The waves are propagated through the wall of the container, then reflected at the interface between the liquid and the container. Accordingly, the thickness of material comprising the container will affect the process. Generally a wall thickness of at least about 1–2 mm will be needed to obtain an accurate viscosity measurement. While there is no theoretical upper limit to the thickness of the container, a practical upper limit to the thickness of the wall of the container is about 150–200 mm (about 6 inches). As the thickness increases, the energy of the ultrasonic pulse generated should be increased or the frequency should be reduced in order to provide for penetration of the ultrasonic wave. The preferred range of wall thickness is 0.25"–3.00", more preferably 0.3– 2.0", even more preferably 0.5–1.0" but depends, in part on the nature of the wall material.

The type of material which makes up the wall of the container will also have an effect on the process. A material which is dense will propagate a wave better and is preferred. A porous, or less dense material can also function as the material for the container, however, the intensity of the reflected wave signal will be diminished. Preferred suitable materials are graphite, molybdenum, aluminum, high density ceramics, steel, glass, plastic and concrete. If the material of the container is insufficient to generate or effectively propagate an ultrasonic wave, a "plug" or a wedge of a suitable material such as steel, glass, plastic or concrete may be attached to the wall of the container, which can be used to generate an ultrasonic wave pulse.

The temperature of the material of the container will also affect the propagation of the ultrasonic wave. Accordingly, the process should be calibrated to account for the temperature of the material. Since the longitudinal wave generated by the laser ultrasound is relatively insensitive to viscosity, the reflection of the longitudinal wave can be used to determine the density and the temperature of the material of the container. In this fashion, since both longitudinal and shear waves are generated by the laser pulse, detection of the reflected longitudinal wave can be used to provide an internal calibration for the temperature and density of the container material.

The reflected wave may be detected by conventional detection means known to those of ordinary skill in the art for the detection of Ultrasonic waves. Non-limiting examples include a laser interferometric detection system, an electromagnetic acoustic transducer (EMAT) or a piezoelectric transducer. A laser interferometric detection system is preferred.

The detection means should be isolated from external vibrations in order to obtain accurate results. Preferably the detection means is isolated from the container containing the material.

According to the present method a pulse laser is focussed at the surface of a container containing a liquid and/or molten material. A laser ultrasonic wave (LUW) of a broad frequency range is generated at the surface of the container wall. This wave travels through the container wall into a molten material. The ultrasonic signal is processed to predict the viscosity of the material. LUW is reflected from the container/air and container/liquid and/or molten material interfaces. The reflected signal from the container/air may be used for the calibration.

Figure 4:
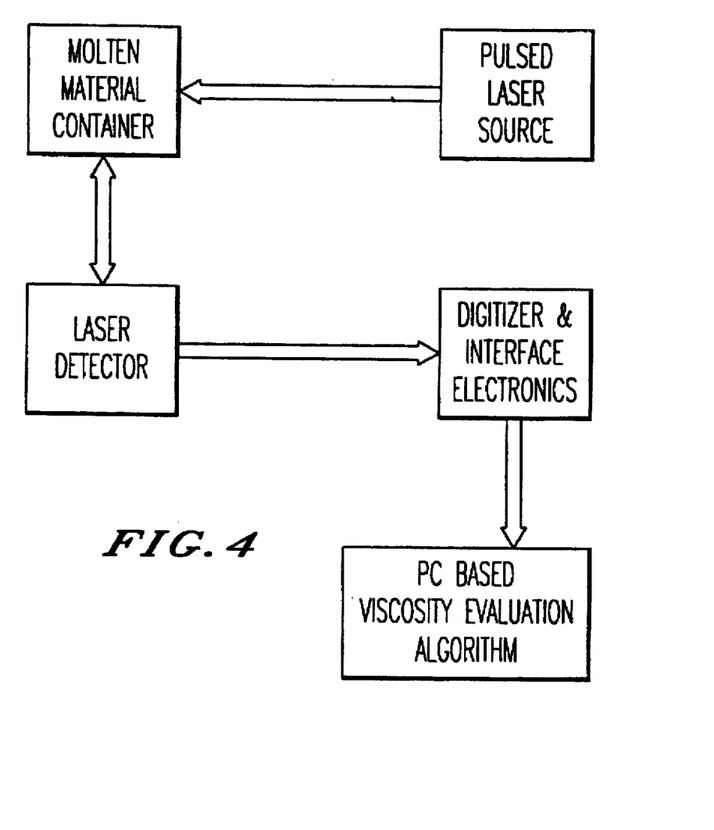
FIG. 4 provides a schematic diagram of specific instrumentation which can form the elements of an apparatus according to the present invention.
Figure 5:
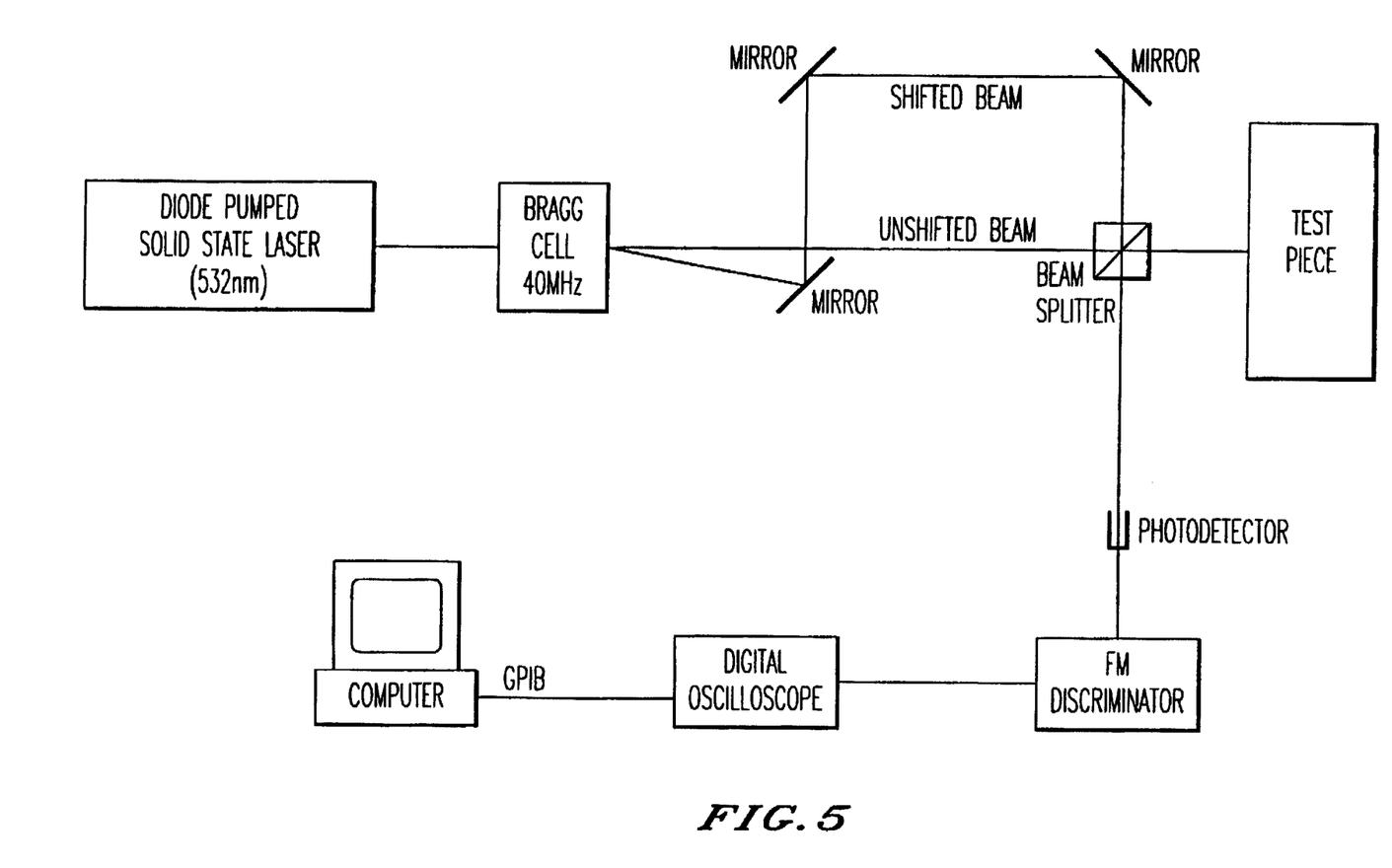
FIG. 5 represents a typical laser interferometer which can be employed to detect ultrasound for the viscosity measurement described.

A laser interferometric based detection system can be used to monitor the LUW from the various interfaces. A narrow line width continuous wave (CW) laser beam is aligned at a selected location on the melt container. The reflected/scattered light is passed through an interferometer and detected by a photo detector. The other scheme such as LUW attenuation is also used in the inversion algorithm. The system diagram (see FIG. 4) shows the instrumentation used in this technique.

The viscosity of a material may be determined on the basis of a reflected wave generated from a single ultrasonic pulse. However, from the standpoint of precision, it is preferable to conduct multiple measurements, averaging the results, if necessary.

Ultrasonic waves may be generated and detected in single measurements, multiple sequential measurements or by continuous generation of ultrasonic waves.

In a preferred embodiment, the signal which is detected by the detection means is digitized by a digitizing interface means. Suitable digitizing interface means are those conventionally known to those of ordinary skill in the art. Non-limiting examples of suitable digitizing interface means include an analog-digital converter, operating at a resolution $\geq 8$ bit, and preferably $\geq 12$ bit, a transient digitizer and a digital oscilloscope with a storage capacity. Suitable digitizing interface means should operate at a recording rate of 25M samples/second or faster.

The detected signal, may be processed by conventional means known to those of ordinary skill in the art. From the stand point of speed and convenience, the signal is processed by electronic means such as by a computer, especially a personal computer.

The reflected wave signal can be processed in several different ways to obtain information about the viscosity of the material. For example, a compressional wave is sent out by the transducer and reflected back at the wedge/fluid boundary. In accordance with the invention, the reflection coefficient is calculated and related to the acoustic impedance of the fluid which is a product of density and sound speed.

For an incident plane horizontally polarized shear wave incident on the solid/fluid interface at an angle $\theta_s$, the real part of the shear reflectance gives a relation between the phase difference and the absolute reflection factor;

$$1-2 \cdot r^2 \cdot (1+2 \cdot \sin^2(\Phi)) + r^4 = 0 \qquad 1$$

The imaginary part gives the relation between viscosity, phase difference and the absolute reflection factor as;

$$\eta = \frac{2 \cdot \rho_s^2 \cdot c_s^2}{\pi \cdot \rho \cdot f} \cdot \frac{\cos^2(\phi_1)}{\cos^2(\phi_t)} \cdot \frac{r \cdot \sin(\Phi) \cdot (1-r^2)}{(1+r^2+2 \cdot r \cdot \cos(\Phi))^2} \qquad 2$$

This requires the measurement of either the absolute reflection factor or the phase difference to be taken to obtain the viscosity of the fluid.

The A'AB method of computing reflection factors may be adopted. In this method the reference signal is $A_{ref}'$ obtained using a stress free interface (air) as a reference. Then the interface is loaded with the fluid and the signal reflecting from the solid-fluid interface is obtained as $A_{fluid}$. The notch gives a constant reference for either of the two measurements ($A_{ref}'$, $A_{fluid}$). The compensating signals ($C_{ref}'$, $C_{fluid}$) are used to compensate for variations in the input.

DC elimination may be used to remove the DC offset from these signals. Using standard Fast Fourier Transform routines, the frequency spectrums of these signals are obtained. To stay in the region with a good signal to noise ratio, a 6 dB down bandwidth is preferably considered for the viscosity spectrum. The absolute reflection factor and phase difference spectrums are obtained using the following:

$$|r(\omega)| = \frac{A_{fluid}(\omega)}{A_{ref}(\omega)} \cdot \frac{C_{ref}(\omega)}{C_{fluid}(\omega)} \qquad 3$$

$$\Phi(\omega) = \phi_{ref}(\omega) - \phi_{fluid}(\omega) + \psi_{fluid}(\omega) - \psi_{ref}(\omega) \qquad 4$$

In the absolute reflection method, also termed as the magnitude spectrum method, the absolute reflection factors are computed from equation 3. The phase information is obtained using the equation 5 as follows:

$$\phi(\omega) + \frac{1}{2} \cdot \cos^{-1}\left(1 - \frac{1 - r(\omega)^2)^2}{2 \cdot r(\omega)^2}\right) \quad 5$$

Similarly in the phase difference approach, the phase is obtained from the experimental data and equation 4. The absolute reflection factors are then computed from the phase using equation 1, noting that $r^2 \in R$. Also, since the reflection factor constitutes the amount of energy reflected back $r \leq 1$. A special case would be the perfect impedance match where r=0. So r is bounded in [0,1]

$$r(\omega) = \pm (1 - 2 \cdot \sin^2(\phi(\omega)) \pm \sin(\phi(\omega)) \cdot \sqrt{1 + \sin^2(\phi(\omega))})^{1/2} \quad 6$$

On solving equation 6, four roots of the equation are obtained, three of which are eliminated using the above arguments.

Figure 6:
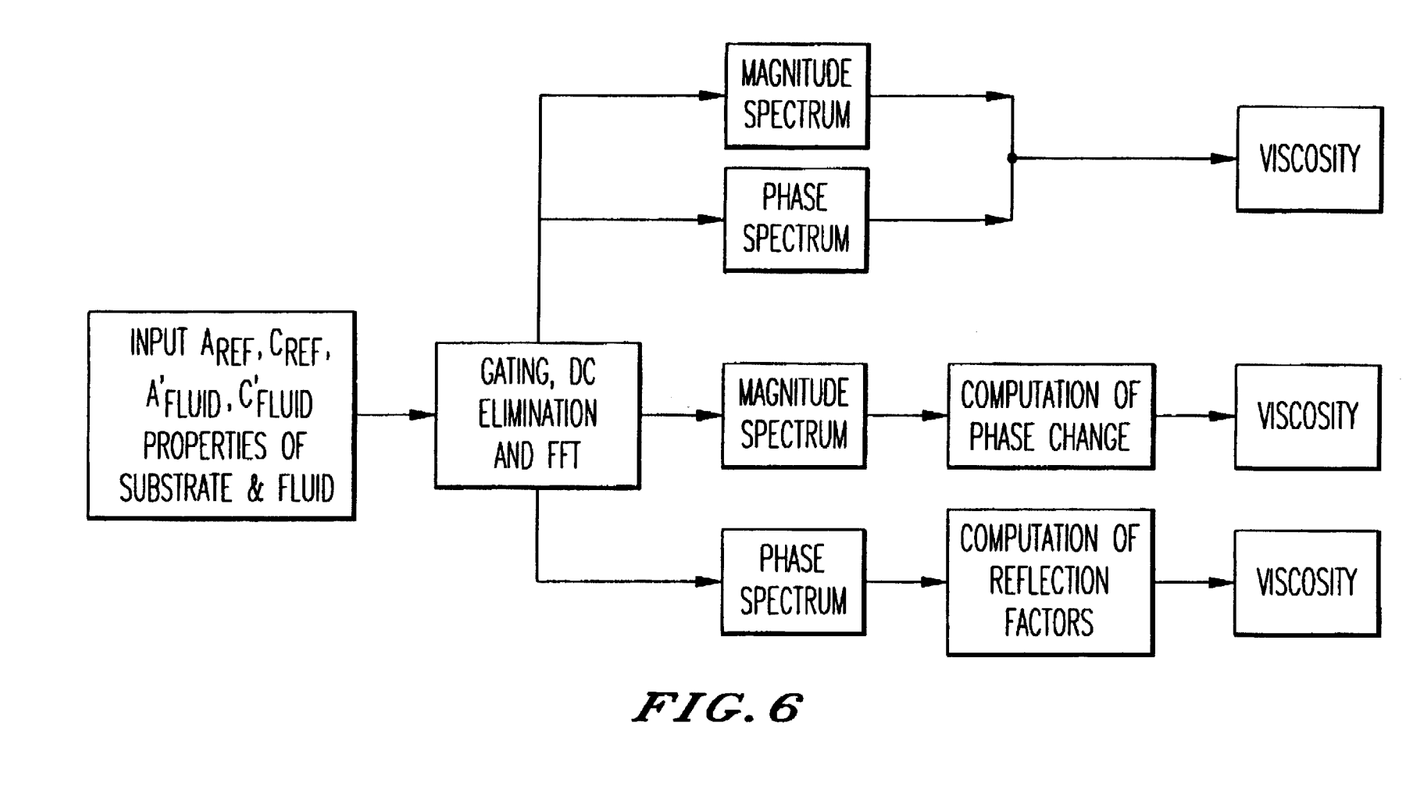
FIG. 6 provides a block diagram for the data processing of the ultrasonic signals and computation of viscosity FIG. 7 provides a schematic diagram of a typical setup for measuring viscosity with laser ultrasound.

A third approach is to consider the effects of the phase difference and magnitude spectrum simultaneously. In this method, the absolute reflection factor spectrum and the phase difference spectrum are obtained from equations 3 and 4. The FIG. 6 represents the various methods for analysis of the ultrasonic data for obtaining the reflection factor from which the viscosity is measured.

The present method is effective at detecting the viscosity of materials over a broad range of viscosities. However, the laser ultrasonic method is more sensitive in detecting a viscosity from 0 to about 400–500 poise. Between the range of about 500 to 5,000 poise, the present method is effective, but less effective than at the lower viscosities. At a viscosity of greater than 5,000 poise, the present method is not as accurate. Accordingly, the viscosity of the material being measured is preferably from 0 to 5,000 poise.

The reflected wave may be monitored for amplitude, phase, and frequency, and a combination of these parameters may be used to determine the viscosity of the material.

The material being measured is not particularly limited in terms of the degree of flow. More specifically, the present method is applicable to a stirred or agitated material as well as to a material flowing through a pipe. However, it is preferably that the material being detected have little or no air bubbles, as air bubbles may affect the reflected waves and therefore the viscosity determination. Accordingly, if a material to be measured contains air bubbles, it may be advantageous to conduct multiple measurements.

This in situ monitoring method can be used in industries involved in the manufacturing and processing of metals, alloys, glass, polymers, textiles, etc., composite materials processing such as the extrusion, and protrusion of molten materials, and also the emerging melter technology for processing various hazardous waste. Viscosity measurement is critical in assuring the quality of the end product in the above industries. The real time measurement of viscosity provides an important parameter to control of the operation of a melter. This will improve the quality of the end product such as glass and alloys.

Figure 1:
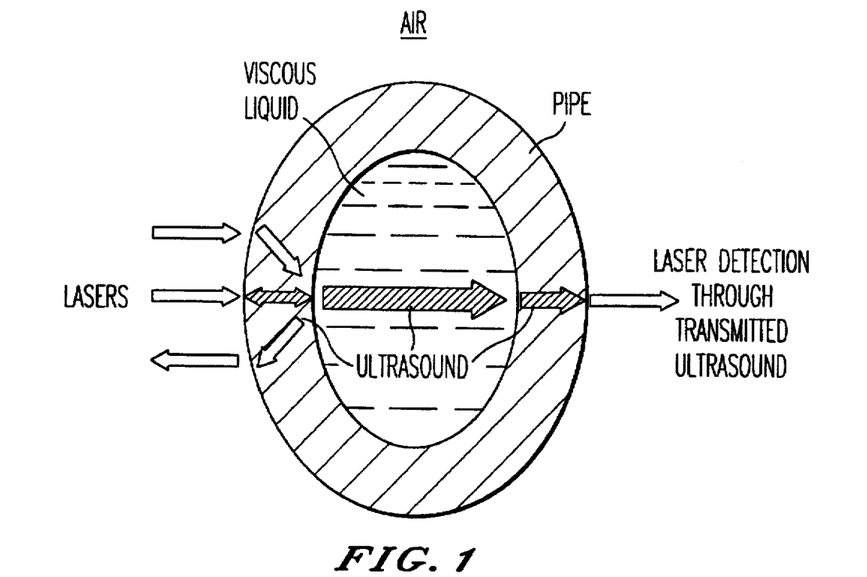
FIG. 1 illustrates the application of laser ultrasound viscometry to a liquid in a pipe.
Figure 2:
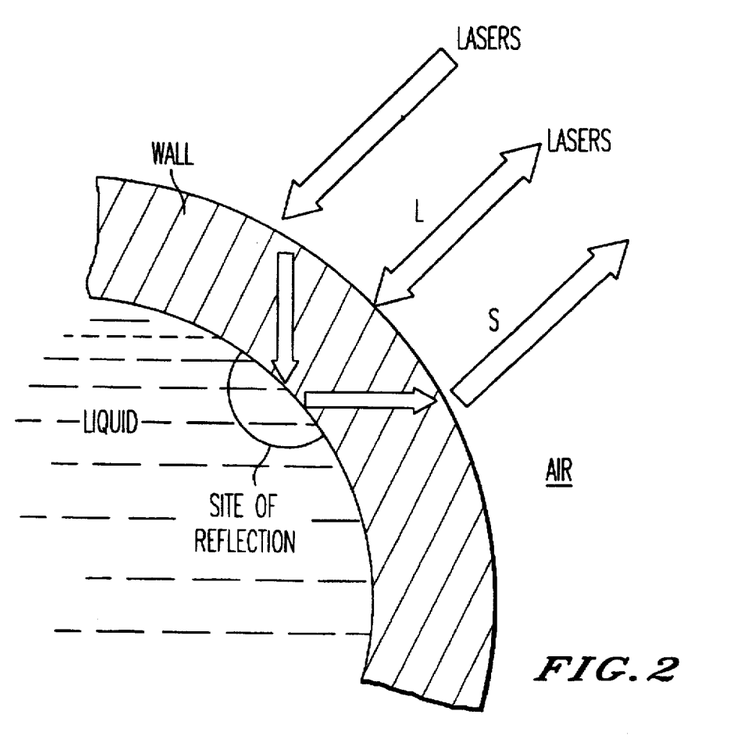
FIG. 2 illustrates the application of laser ultrasound viscometry to a liquid in a tank.
Figure 3:
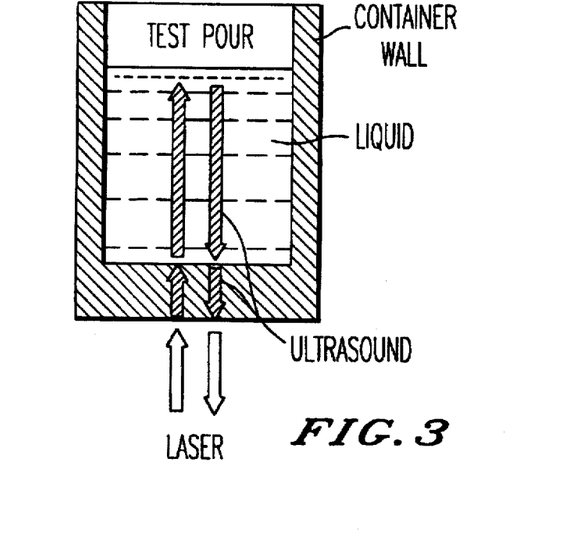
FIG. 3 illustrates the application of laser ultrasound viscometry to a liquid in a small test pour container.

This technique allows the measurement of the viscosity in a wide range of industrial applications such as in pipes (FIG. 1), in tanks (FIG. 2), in small test pour containers (FIG. 3), etc.

Having generally described this invention, a further understanding can be obtained by reference to certain specific examples which are provided herein for purposes of illustration only and are not intended to be limiting unless otherwise specified.

Figure 7:
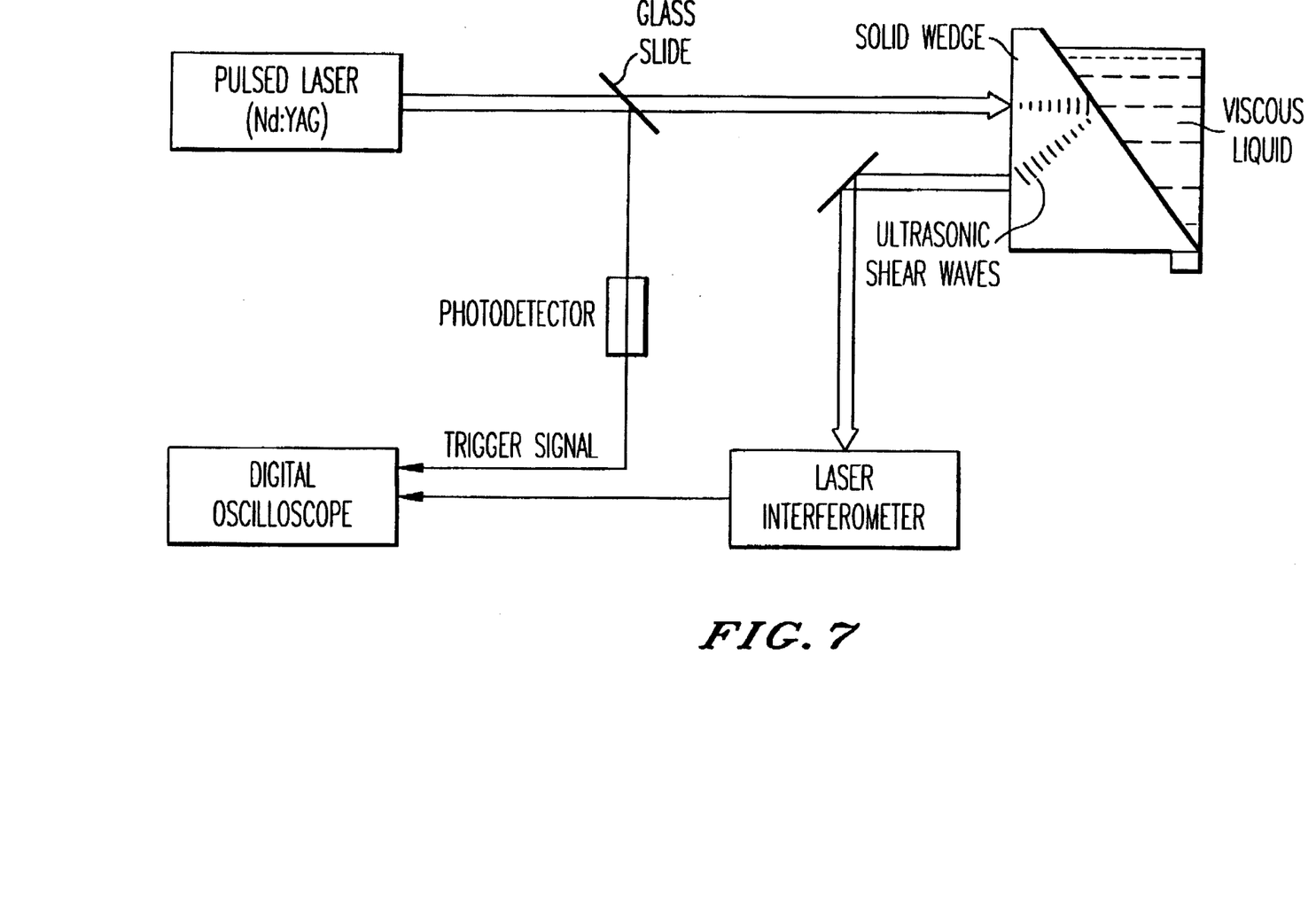
Figure 8:
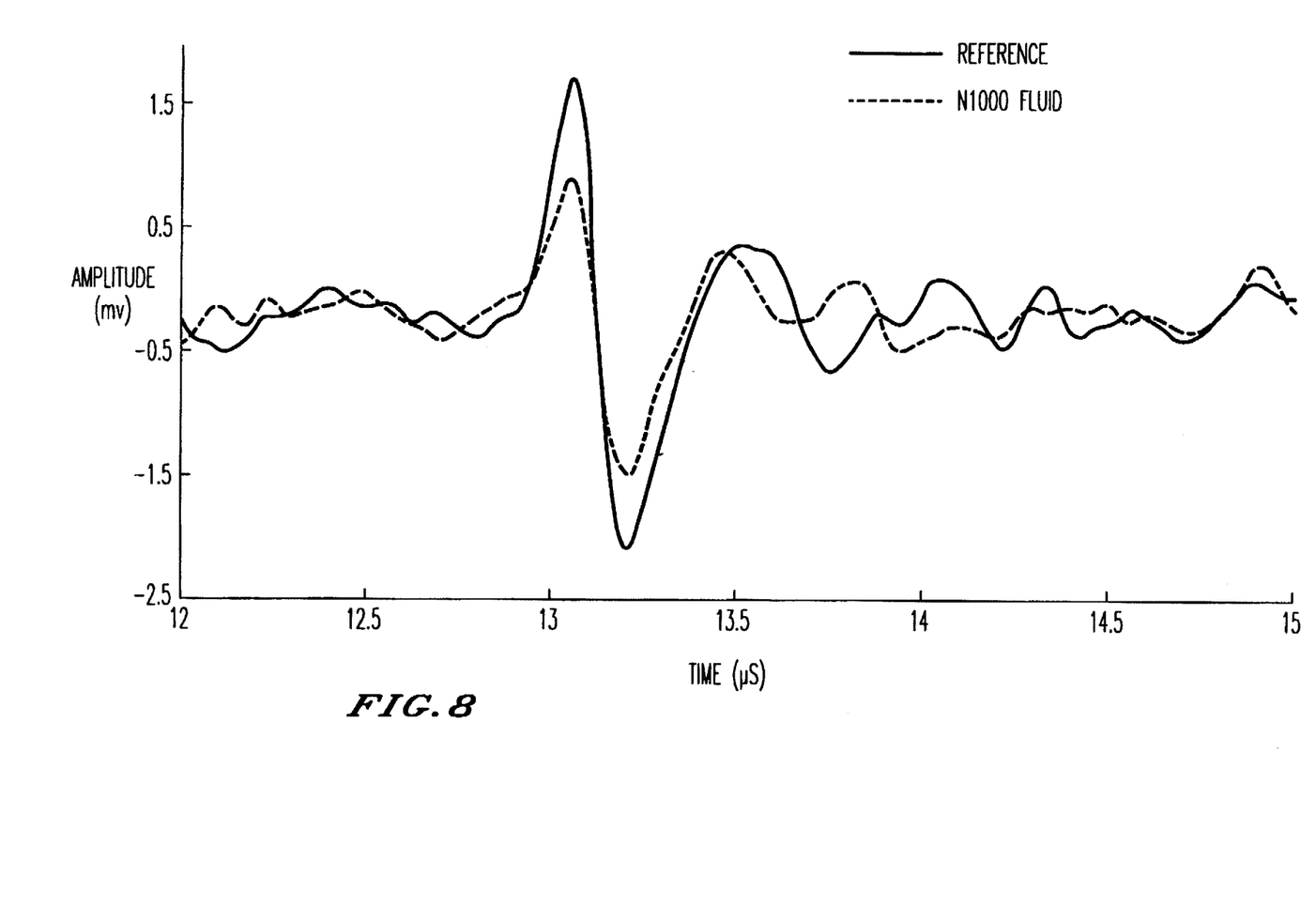
FIG. 8 depicts the amplitude over time of a reflected laser shear wave in carbon.
Figure 9A:
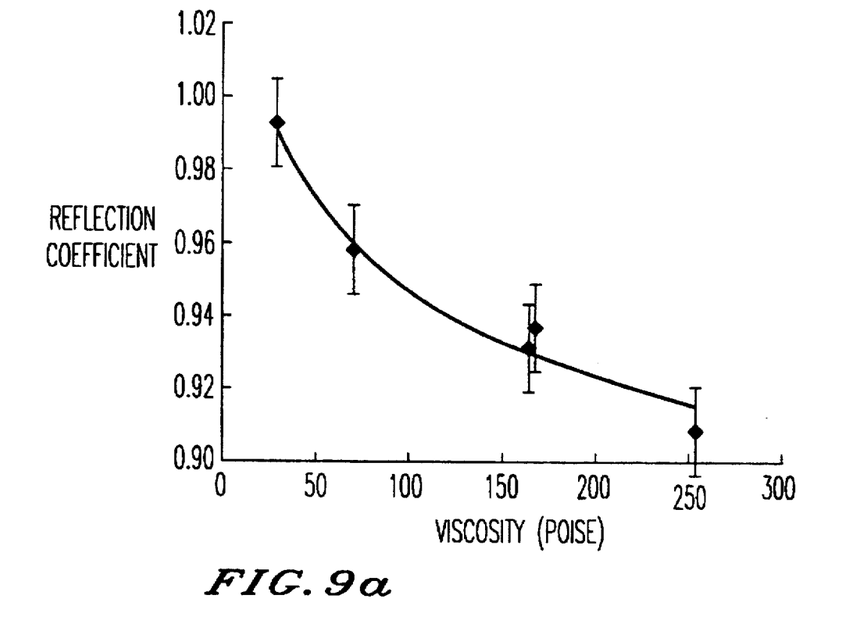
FIG. 9a shows the reflection factor platted as a function of viscosity of a liquid measured in an aluminum solid.
Figure 9B:
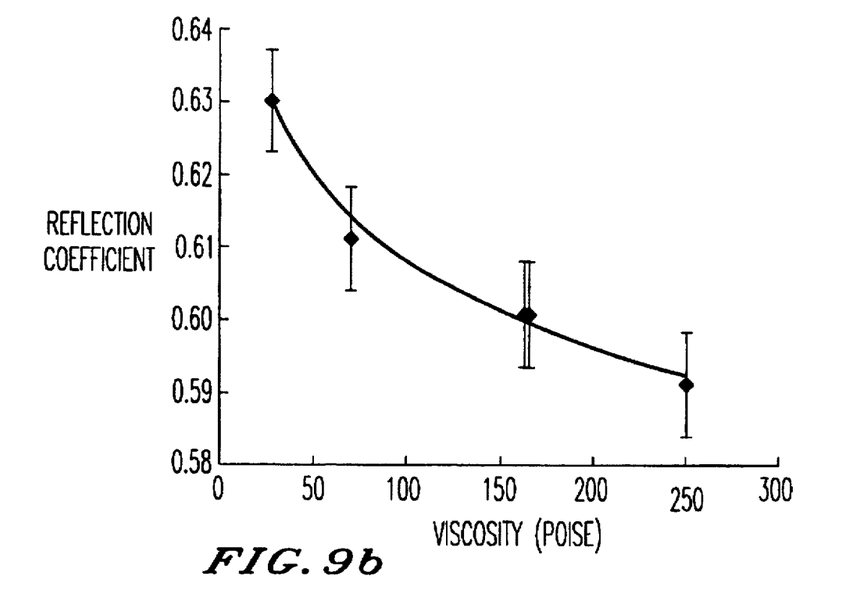
FIG. 9b shows the reflection factor plotted as a function of viscosity of a liquid measured in a graphite solid.

A typical experiment conducted in the laboratory is illustrated in FIG. 7. This consists of a Nd-YAG laser which is Q-switched to generate 10 pulses per second. The pulsed laser beam strikes a solid wedge and generates shear waves within the solid wedge. The ultrasound travels within the solid media and reflects at the solid-viscous liquid media interface and the reflected ultrasound shear wave is detected by an interferometer again at the outer surface of the solid wedge. A photo-detector is also used to trigger the digital oscilloscope. The signal from the interferometer is digitized and is stored for analysis using a PC. A set of typical signal is displayed in FIG. 8. Here, the reference RF signal, which is the signal with the high amplitude is the signal obtained from the solid-air interface (when there is no viscous liquid in contact with the solid). The reflected RF ultrasound signal from the 10 Poise viscous fluid (NIST traceable viscous liquid obtained from Cannon Inc., PA, U.S.A.) is overlaid on the reference RF signal. The decrease in the reflected signal is clearly noticeable. The ratio of the peak to peak amplitude of the reflected signal to that obtained from the reference signal will provide the absolute reflection factor. FIGS. 9 (a and b) show the reflection factors plotted as a function of viscosity of the liquids for two solid media (FIG. 8a is for Aluminum and FIG. 8b is for Graphite) with the error bars.

Obviously, additional modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method of determining the viscosity of a molten material comprising:
    (a) transmitting ultrasonic waves produced by a pulsed laser through a container containing a molten material;
    (b) detecting the frequency and a wave component selected from the group consisting of amplitude, phase or amplitude and phase of the reflected waves;
    (c) determining the viscosity of said molten material based on detection of said reflected waves
    wherein ultrasonic waves of a frequency of from 100 kHz–30,000 KHz are used.

2. The method of claim 1, wherein said pulsed laser supplies a pulse energy of 10 millijoules–10 joules.

3. The method of claim 1, wherein said pulse laser supplies pulses of a duration of from 1 nanosecond to 10 microseconds.

4. The method of claim 1, wherein said reflected waves are detected by a detection system selected from the group consisting of a laser interferometer system, an electromagnetic acoustic transducer or a piezoelectric transducer.

5. The method of claim 1, wherein said molten material has a viscosity of from 0–5,000 poise.

6. The method of claim 1, wherein said molten material is selected from the group consisting of metal, alloys, glass, polymers, textiles and a hazardous waste.

7. An apparatus for determining the viscosity of a molten material comprising:
    i) a pulsed laser source for producing ultrasonic longitudinal and shear waves at a frequency of from 100 KHz–30,000 KHz, in a molten material:

ii) a detection system for detecting reflected longitudinal and shear waves from said molten material; and iii) a processing means for determining a viscosity of a molten material based on detected reflected longitudinal and shear waves.

8. The apparatus of claim 7, wherein said pulsed laser source is a laser selected from the group consisting of $CO_2$, krypton fluoride, neodymium yttrium-aluminum garnet (YAG), ruby, titanium sapphire, aluminum gallium arsenide, indium gallium arsenide phosphide, aluminum indium gallium phosphide, and a dye laser.

9. The apparatus of claim 7, wherein said detection system is selected from the group consisting of a laser interferometric detection system, an electromagnetic acoustic transducer (EMAT) and a piezoelectric transducer.

10. The apparatus of claim 7, wherein said detection system is a laser interferometric detection system.

11. The apparatus of claim 7, further comprising:

iii) means for digitizing an ultrasound signal.

12. The apparatus of claim 11, further comprising:

iv) means for processing a digitized signal.

13. The apparatus of claim 11, wherein said means for digitizing an ultrasound signal is selected from the group consisting of an analog-digital converter, a transient digitizer and a digital oscilloscope with a storage capacity.

14. The apparatus of claim 13, wherein said analog-digital converter is operated at a resolution $\geq 8$ bit.

* * * * *

UNITED STATES PATENT AND TRADEMARK OFFICE
CERTIFICATE OF CORRECTION

PATENT NO. : 5,686,661
DATED : November 11, 1997
INVENTOR(S) : Jagdish P. Singh et al.

It is certified that error appears in the above-identified patent and that said Letters Patent is hereby corrected as shown below:

Column 1,
After the title please insert the following:

-- This invention was made with U.S. Government support under contract number DE-FG02-93CH10575 awarded by the Department of Energy. The U.S. Government may have certain rights in this invention. --

Signed and Sealed this

Fourth Day of December, 2001

Attest:

NICHOLAS P. GODICI
Attesting Officer   Acting Director of the United States Patent and Trademark Office